United States Patent [19]

Tsarev et al.

[11] Patent Number: 5,476,658
[45] Date of Patent: Dec. 19, 1995

[54] VACCINE AGAINST HEPATITIS A COMPRISING SIMIAN HAV ISOLATE AGM-27

[75] Inventors: Sergie A. Tsarev, Bethesda; Suzanne U. Emerson, Rockville, both of Md.; Michael S. Balayan, Moscow, U.S.S.R.; Robert H. Purcell, Boyds, Md.

[73] Assignee: The United States of America as represented by the Department of Health and Human Services, Washington, D.C.

[21] Appl. No.: 674,852

[22] Filed: Mar. 26, 1991

[51] Int. Cl.$^6$ .......................... A61K 39/29; C12N 15/51; C07K 14/10
[52] U.S. Cl. ................. 424/226.1; 424/184.1; 424/204.1; 424/225.1; 424/189.1; 536/23.72; 514/2; 435/69.3; 435/235.1; 435/236; 435/237; 530/350; 530/825
[58] Field of Search ..................... 424/89, 189.1, 424/204.1, 184.1, 225.1, 226.1; 435/235.1, 235.1, 236, 237; 536/27, 23.72; 514/2; 530/350, 826

[56] References Cited

U.S. PATENT DOCUMENTS 4,894,228  1/1990  Purcell ........................ 424/89

OTHER PUBLICATIONS

Provost, P. J. et al. J. Med. Virol 20: 165–175 (1986).
Karron, R. A. et al. J. Infect. Dis. 157(2): 338–345 (1988).
Tsarev, S. A. et al (91) J. Gen. Virol. 72:1677–1683.
Brown, E. A. et al. (89) J. Virol. 63:4932–4937.
Lemon, S. M. et al. (87) J. Virol. 618:735–742.
Balayan, M. S. et al. (1989) FEBS Letters 247: 425–428.
Andzhaparidze, A. G. et al (1987) Vopr. Virus 6: 681–686.
Cohen, J. I. et al (1989) J. Virol. 63: 5364–5370.

*Primary Examiner*—Christine M. Nucker
*Assistant Examiner*—Michael S. Tuscan
*Attorney, Agent, or Firm*—Morgan & Finnegan

[57] ABSTRACT

The present invention relates, in general, to a substantially pure preparation of the simian hepatitis A viral isolate AGM-27; a substantially pure preparation of the genomic DNA of simian hepatitis A viral isolate AGM-27; a pharmaceutical composition comprising the simian hepatitis A viral isolate AGM-27; a method of preventing hepatitis A in an animal; and a vaccine comprising the simian hepatitis A viral isolate AGM-27.

6 Claims, 6 Drawing Sheets

FIG. 3A

```
                                        <VP4
                                 M    N    M   --
HM-175 --  CTT  AA-  ---  ATA  ATA  ATG  AAC  ATG --
            ..   ..        ..   ..  ...   ..  ...
            ..   ..        ..   ..  ...   ..  ...
AGM-27 --  TAT  ATG  TTT  ATG  ATG  ATG  AAT  ATG --
            M    F    M    M    M    N    M  --
                 <VP4
```

FIG. 3B

```
                    70
           --   S    D    S   --
HM-175 --  TCA  GAC  TCA --
            ..   .    ..
            ..   .    ..
AGM-27 --  TCT  GCA  TCT --
           --   S    A    S   --
```

FIG. 3C

```
                   102
           --   N    S    N   --
HM-175 --  AAT  TCA  AAT --
           ...   ..   ..
           ...   ..   ..
AGM-27 --  AAT  GCA  AAC --
           --   N    A    N   --
```

FIG. 3D

```
              VP3><VP1
           --   T    Q    V    G   --
HM-175 --  ACA  CAA  GTT  GGA --
            ..   ..        ..
            ..   ..        ..
AGM-27 --  TCA  CAG  ACA  GGT --
           --   S    Q    T    G   --
```

FIG. 6

Infectious cDNA of HM-175 in pGEM

SP6 → 5'
Sac I
Eco RI
3'

P2 region (2A, 2B, 2C)

↓ Sac I / EcoRI

SP6 → 5'
Sac I
Eco RI
3'

PCR fragment from AGM-27

Sac I — Sac I — Sal I — EcoRI
← 330 b.p. → ← 980 b.p. →
← 1700 b.p. →

Eco RI + partial Sac I

↓ ligation

SP6 → 5'
Sac I
Sac I
Sal I
Eco RI
3'

P2 region (2A, 2B, 2C from AGM-27)

VACCINE AGAINST HEPATITIS A COMPRISING SIMIAN HAV ISOLATE AGM-27

BACKGROUND OF THE INVENTION

1. Field of the Invention

The present invention relates, in general, to a hepatitis A virus. In particular, the present invention relates to a simian hepatitis A viral isolate AGM-27 as deposited with the American Type Culture Collection, 12031 Parklawn Drive, Rockville, Md., on Aug. 24, 1992 and having American Type culture Collection (ATCC) accession Number VR2380.

2. Background Information

Hepatitis-A virus (HAV) is a significant human pathogen that is spread via the fecal-oral route. HAV is a picornavirus that is endemic in underdeveloped areas of the world and causes 20–25% of clinical hepatitis in the developed countries.

Hepatitis A virus has been recovered from several species of New or Old World monkeys. It is not clear whether these isolates are true simian strains or human strains that have infected primates in captivity. Human strains can produce acute hepatitis in some higher primates such as the chimpanzee (Dienstag, J.L., et al. (1975) J. Infect. Dis. 132:532–545), marmoset (*Saguinus species*) (Deinhardt, F., et al. (1975) Amer. J. Med. Sci. 270:73–80) and owl monkey (*Aotus trivigatus*) (LeDuc, J.W., et al. (1983) Infect. Immun. 40:766–772), but only one group has reported that an Old World monkey (stump-tailed monkey, *Macaca speciosa*) (Mao, J.S., et al. (1981) J. Infect. Dis. 144:55–60) has developed acute hepatitis after experimental infection. An important question is how different human and simian isolates actually are.

Recently, comparison of partial genome sequences for two simian strains isolated respectively from an owl monkey (Brown, E.A., et al. (1989) J. Virol. 63:4932–4937) and a cynomolgus monkey (*Macaca fascicularis*) (Balayan, M.S., et al. (1989) FEBS Lett. 247:425–428) revealed that these two simian strains differed greatly from human HAVs in the limited regions examined. The present invention provides the almost complete sequence of a simian HAV obtained from an African green monkey. Extensive sequence differences between this isolate and other simian and human strains are to be noted. In addition, it can be seen that the simian wild-type strain differs from a human wild-type strain in its ability to grow in simian cell cultures.

SUMMARY OF THE INVENTION

It is a general object of this invention to provide a hepatitis A viral isolate.

It is a specific object of this invention to provide the simian hepatitis A viral isolate AGM-27.

It is another object of the invention to provide genomic DNA of the simian hepatitis A viral isolate AGM-27.

It is a further object of the invention to provide a pharmaceutical composition comprising the simian hepatitis A viral isolate AGM-27.

It is another object of the invention to provide a method of preventing hepatitis A in an animal.

It is a further object of the invention to provide a vaccine comprising the simian hepatitis A viral isolate AGM-27.

Further objects and advantages of the present invention will be clear from the description that follows.

BRIEF DESCRIPTION OF THE DRAWINGS

FIGS. 3A–3D show some of the important differences between human strain HM-175 and AGM-27. These differences include an extension of the open-reading frame in the translation-initiation region (FIG. 3A); replacement of D-70 by A-70 in the VP3 region (FIG. 3B); replacement of S-102 by A-102 in the VP1 region (FIG. 3C) and a change of the cleavage site from Q-V to Q-T in the VP2-VP1 junction (FIG. 3D).

FIG. 5A shows transmission to African Green Monkeys, FIG. 5B shows transmission to marmoset monkeys and FIG. 5C shows transmission to chimpanzees.

FIG. 6. Construction of Chimeric HAVs between human and simian strains.

DETAILED DESCRIPTION OF THE INVENTION

Figure 1:
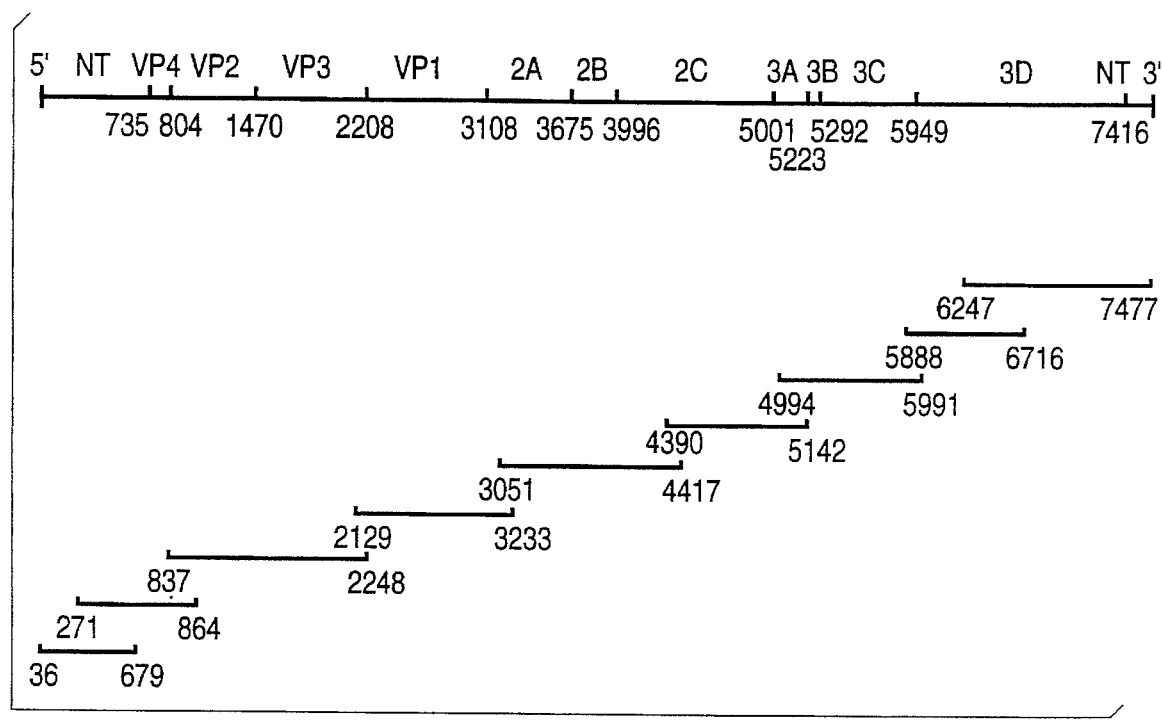
FIG. 1. Scheme of HAV genome and PCR fragments obtained from AGM-27. Nucleotide numbers are based on the genomic map of HM-175 (Cohen, J.I., et al. (1987) J. Virol. 61:50–59). The sizes of PCR fragments shown include the length of oligonucleotide primers.

The present invention relates to a simian hepatitis A viral isolate.

In one embodiment, the present invention relates to a substantially pure preparation of the simian hepatitis A viral isolate AGM-27. The virus was isolated in primary African Green Monkey Cells shown to be free of contaminatin viruses and is therefore suitable for oral administration after completion of requisite safety tests. The fact that none of the strains of hepatitis A virus isolated from man until now has characteristics similar to those of AGM-27 and tests in several primate species indicates that this strain will be attenuated for in humans. Therefore, this strain can be expected to be suitable for use as a live vaccine against hepatitis A. Transmission experiments in primates can be used to determine whether this strain can cross-protect against wild type human strains.

In another embodiment, the present invention relates to a substantially pure preparation of the genomic DNA of simian hepatitis A viral isolate AGM-27. In one preferred embodiment, the genomic DNA has the sequence shown in SEQ ID NO:1.

In a further embodiment, the present invention relates to a pharmaceutical composition comprising the above-described simian hepatitis A viral isolate AGM-27 in an amount effective to prevent hepatitis A in an animal, and a pharmaceutically acceptable diluent, carrier, or excipient. The pharmaceutical composition of the invention includes the viral isolate AGM-27 in a quantity selected depending on the route of administration (preferably, oral (P.O.), subcutaneous, I.M., or I.V.). Appropriate concentrations and dosage unit sizes can be readily determined by one skilled in the art. Suitable amounts might be expected to fall within the range of approximately $10^3$ to approximately $10^8$ tissue culture infectious doses.

In another embodiment, the present invention relates to a method of preventing hepatitis A in an animal comprising administering to the animal the above-described simian hepatitis A viral isolate AGM-27 under conditions such that said hepatitis A is prevented. One skilled in the art will appreciate that the amounts to be administered for any particular treatment protocol can readily be determined.

In a further embodiment, the present invention relates to a vaccine comprising the above-described simian hepatitis A vital isolate AGM-27 in an amount effective to prevent hepatitis A in an animal and a pharmaceutically acceptable diluent, carrier, or excipient. In one preferred embodiment, the animal is selected from the group consisting of humans, apes, and monkeys.

It has been demonstrated that attenuation of one isolate of virulent HAV occurred in parallel with its adaptation to growth in cell culture. Wild-type HAV isolated from clinical materials grows extremely poorly in cell culture: in vivo replication usually cannot be detected in primate cells until 10–12 weeks after inoculation. It is interesting, therefore, to find that wild type simian HAV grows in primary AGMK cells or the FRhK-4 cell line without prior adaption. While its ability to grow directly in FRhK-4 or AGMK cells distinguished AGM-27 from the wild-type HM-175, its inability to grow in CV-1 cells distinguished it from the cell culture-adapted variant of the human virus.

These structural and biological data demonstrate that the AGM-27 strain differs significantly from any other known strains of HAV and is a good model for further investigation of the molecular basis of HAV cell-culture adaptation and attenuation. The genome of AGM-27 differs from those of human strains in approximately 1400 nucleotide positions while the human wild-type and attenuated strains of HM-175 differ only in 24 nucleotide positions. A live vaccine based on the AGM-27 strain can be expected to be significantly safer in terms of low reversion to a virulent strain. Thus, chimeric viruses between a human attenuated strain and AGM-27 strain can be designed. These chimeras will have structural regions from the human strain in order to have immunogenic properties of human viruses and nonstructural regions from AGM-27 (especially 2B, 2C and 5' end non-coding region; see Emerson, S.U. et al. (1989) In: R.A. Lerner et al (eds) Modern approaches to new vaccines including prevention of AIDS, Cold Spring Harbor Laboratory, pp. 427–430).

The present invention is described in further detail in the following non-limiting examples.

EXAMPLES

The following protocols and experimental details are referenced in the examples that follow:

HAV. The AGM-27 isolate was obtained as a 10% wt/vol liver homogenate in phosphate buffered saline (pH 7.2) from a clinically-ill African green monkey that was naturally infected with hepatitis A virus in a facility for housing primates (Andzhaparidze, A.G., et al. (1987) Vopr. Virus 6:681–686).

Primers. Eighty oligonucleotides, 15 nucleotides in length and previously synthesized for sequencing human HAV HM-175 (Cohen, J.I., et al. (1987) J. Virol. 61:50–59; Cohen, J.I., et al. (1987) Proc. Natl. Acad. Sci. USA 84:2497–2501), were used for PCR and sequencing reactions. Forty-eight new primers, 19–24 nucleotides in length and complementary to plus or minus strands of the AGM-27 genome, were synthesized using an Applied Biosystems 391 DNA Synthesizer.

Preparation of virus RNA template for PCR. One-half ml of 10% liver homogenate from African green monkey 27 (Andzhaparidze, A.G., et al. (1987) Vopr. Virus 6:681–686), 20% SDS (to a final concentration of 1%) and 10 mg/ml proteinase K (to a concentration of 1 mg/ml) were mixed and incubated for 30 min at 55° C. Total nucleic acids were extracted with phenol at 65° C., precipatated by ethanol, and stored in ethanol at –80° C.

Preparation of virus RNA template for PCR of 5' end. Thirty ml of 10% liver homogenate was clarified by centrifugation at 3,000 rpm for 1 h at 4° C. in a Beckman J-6B Centrifuge. The supernatant was centrifuged at 23,000 rpm in a Beckman SW25 rotor for 14 h. The pellet was resuspended in 1 ml of DNase I buffer with 0.1 mg/ml DNase I and incubated at 37° C. for 30 min. RNA was extracted with phenol at 65° C., treated with RNase-free RQI DNase (Promega Biotec, Madison), and centrifuged at room temperature through 5.7 M CsCl, 10 mM EDTA (pH 7.5) at 40,000 rpm for 14 h in a Beckman SW60 rotor. The RNA pellet was dissolved in 200 µl of water, precipitated with ethanol and stored in ethanol at –80° C.

PCR. Five µl of ethanol-precipitated total nucleic acid or 10 µl of CsCl-purified RNA was centrifuged through 500 µl of ethanol, dried, and used for reverse transcription (RT) and PCR. The usual 100 µl RT-PCR mixture contained template, 10 mM Tris-HCl (pH 8.4), 50 mM KCl, 2.5 mM $MgCl_2$, 0.2 mmol of each dNTP, 1 nmol direct primer, 1 nmol reverse primer, 4 U RNasin (Promega Biotec, Madison), 5 U AMV-RT (Promega Biotec, Madison), 4 U AmpliTaq (Cetus Corp., CA), under 100 µl of light mineral oil. The mixture was incubated 1 h at 42° C., and then amplified by 35 cycles of PCR: 1 min 94° C., 1.5 min at 30°–60° C. depending on primers, 1 to 5 min at 72° C. The products of PCR were analyzed on 1% agarose gels.

Antigen-capture PCR method. AGM-27 viruses from 10% liver homogenate were bound by monoclonal antibodies K2-4F2 or K3-C8 (MacGregor, A., et al. (1983) J. Clin. Microbiol. 18:1237–1243) to 1.5 ml polypropylene microcentrifuge tubes and PCR with primers specific to the VP3 region was performed as described (Jansen, R.W., et al. (1990) Proc. Natl. Acad. Sci. USA 87:2867–2871).

Purification of PCR fragments for sequencing. PCR fragments were cut from 1% agarose gels, purified by using Geneclean (Bio 101, La Jolla, Calif.) and sequenced by using Sequenase (United States Biochemical Corp., Ohio) as described (Winship, P.R., et al. (1989) Nucleic Acids Res. 17:1266).

Computer analysis of sequences. Nucleotide sequences of HAV strains were compared with that of HAV strain AGM-27 by using the global alignment program "GAP" from the "GCG" software package (Devereux, J., et al. (1984) Nucl. Acids. Res. 12:387–395) on a VAX 11/750 computer (Digital Equipment, Landover, Md.). Multiple alignments were made by using the GCG program "PRETTY" TO ensure that sequence gaps introduced by GAP were consistent from strain to strain. Per cent sequence identity was calculated by using the output from GAP and the shorter sequence length as the denominator in the GCG program "DISTANCES."

Amino acid sequences were compared by using the global alignment program "SEQAP" from the "IDEAS" software package (Goad, W.B., et al. (1982) Nucleic Acids Res. 10:247–263). Per cent identity was calculated from the output of SEQAP by using the shorter sequence length as the denominator. Amino acid sequences representing L or VP4 through VP1 and 3B through 3D of HAV strain AGM-27, HAV strain HM-175, encephalomyocarditis virus (Palmenberg, A.C., et al. (1984) Nucleic Acids Res. 12:2969–2985), poliovirus type 1 Mahoney (19; Racaniello, V.R., et al. (1981) Proc. Natl. Acad. Sci. USA 78:4887–4891), foot-and-mouth-disease virus type A12 (Forss, S.K., et al. (1984) 12:6587–6601), rhinovirus type 2 (Skern, T., et al. (1985) Nucleic Acids Res. 13:2111–2126), and rhinovirus type 14 (Callahan, P.L., et al. (1985) Proc. Natl. Acad. Sci. USA. 82:732–736; Stanway, G.P., et al. (1984) Nucleic Acids Res. 12:7859–7875) were compared by using the program "RELATE" (Dayhoff, M.O. (1978) p. 1–8 In Dayhoff M.O., ed. Atlas of protein sequence and structure, vol. 5 suppl. 3. Washington, DC: National Biomedical Research Foundation).

Virus growth in cell cultures. FRhK-4 and CV-1 cell monolayers were incubated with 10-fold serial dilutions of AGM-27 virus (10% liver homogenate) or the HM-175 cell culture-adapted virus. Diluted viruses (0.15 ml) were added to monolayers of CV-1 or FRhK-4 cells, incubated 90 min at 34.5° C. and then 1 ml of DMEM with 10% fetal calf serum was added. After 20 days incubation in a $CO_2$ incubator, 1 ml of 2x proteinase K buffer was added to each well to solubilize the cells. Each well contained approximately the same number of cells as measured by light microscopy and determination of total DNA in cell lysates. RNA was isolated from an 80 µl aliquot by proteinase K digestion followed by phenol extraction and used for slot-blot hybridization (Ticehurst, J.R., et al. (1987) J. Clin. Microbiol. 25:1822–1829) with [$^{32}$P] labeled riboprobe corresponding to the negative strand of the entire HM-175 genome.

EXAMPLE 1

Comparison of the AGM-27 genome sequence with other HAV genomes

The primary structure of the AGM-27 genome was determined from overlapping PCR fragments (FIG. 1). These fragments encompassed the genome corresponding to nucleotides 36–7477 of HM-175 (Cohen, J.I., et al. (1987) J. Virol. 61:50–59). Direct sequencing of these fragments provided AGM-27 sequence between nucleotides 59 and 7458.

The extreme 3' end primer effective in PCR was complementary to the region just before the start of poly A. The extreme 5' end primer effective in PCR corresponded to nucleotide 36–53 of the HM-175 sequence. Five other primers to the region of HM-175 5' to nucleotide 36 were not effective in PCR when used with the AGM-27 genome, although 2 of them were highly effective in PCR of HM-175. Therefore, there may be extensive differences between AGM-27 and HM-175 in the 5' terminus of the genome.

Figure 2:
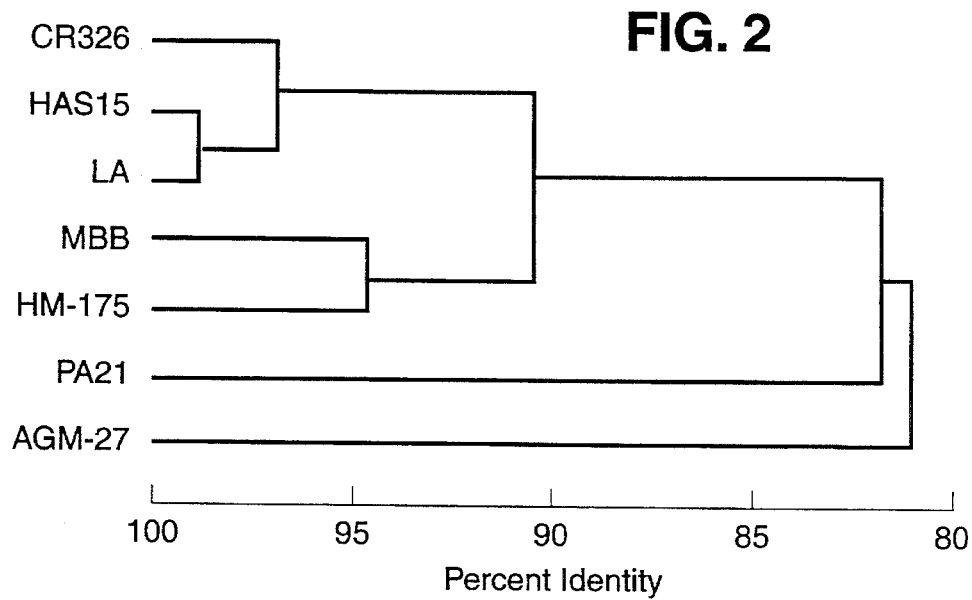
FIG. 2. Per cent identity among HAV nucleotide sequences coding for capsid proteins, calculated by using the programs "GAP" and "DISTANCES" (Devereux, J., et al. (1984) Nucl. Acids. Res. 12:387–395).

Overall, the nucleotide and amino acid sequences of HAV strain AGM-27 are less similar to those of human HAV strains than the human strains are to each other and are no more similar to those of HAV strain PA21, isolated from an owl monkey, than to other HAV strains (Table I, FIG. 2). Statistical analysis performed with the program RELATE (Dayhoff, M.O. (1978) p. 1–8 In Dayhoff M.O., ed. Atlas of protein sequence and structure, vol. 5 suppl. 3. Washington, DC: National Biomedical Research Foundation) indicated that the amino acid sequences of HAV strains AGM-27 and HM-175 representing VP4 through VP1 and 3B through 3D have little similarity to corresponding regions from other picornaviruses; in these regions, HAV strain AGM-27 did not appear to be more similar than HAV strain HM-175 to any particular picornavirus.

In particular, four of the changes noted lead to unique characteristics of the AGM-27 isolate. These important differences between AGM-27 and all other known human and simian HAVs are detailed in FIG. 3A–3D. One of the four changes (FIG. 3b) leads to substitution of Asp-70 with Ala-70 in VP3. This substitution is present in neutralization-resistant mutants of HM-175 that lack the ability to bind monoclonal antibody K2-4F2 but still can bind monoclonal antibody K3-4C8 (Ping, L-H., et al. (1988) Proc. Natl. Acad. Sci. USA 85:8281–8285). Using the antigen-capture PCR technique, specific PCR product was obtained when antibody K3-4C8 was used for the capture but not when K2-4F2 was used (data not shown). The other three critical changes are located in the translation-initiation region (FIG. 3a), in the VP1 region (FIG. 3c) and in the VP2-VP1 junction (FIG. 3d).

TABLE 1

Sequence comparisons of HAV strain AGM-27 and other HAV strains[a]

| Genome region | Length | | | | *Identity versus AGM-27 | | | |
| --- | --- | --- | --- | --- | --- | --- | --- | --- |
| | Nucleotides | | Amino acids | | Nucleotides[b] | | Amino acids[c] | |
| | AGM-27 | others | AGM-27 | others | PA21 | human | PA 21 | human |
| 5'NT | 675[d] | 726–734 | — | — | — | 82.0–84.3 | — | — |
| 1A | 81 | 69 | 27 | 23 | 93 | 90–94 | 96 | 96–100 |
| 1B | 666 | 666 | 222 | 222 | 80.9 | 81.7–82.6 | 97.3 | 96.4–97.7 |
| 1C | 738 | 738 | 246 | 246 | 82.7 | 82.0–83.1 | 95.5 | 96.7–97.2 |
| 1D | 900 | 882–900 | 300 | 294–300 | 77.9 | 80.1–81.4 | 92.7 | 89.3–94.0 |
| 2A | 567 | 567 | 189 | 189 | — | 77.1–81.5 | — | 89.9 |
| 2B | 321 | 321 | 107 | 107 | — | 80.7–83.2 | — | 92.5 |
| 2C | 1005 | 1005 | 335 | 335 | — | 78.3–79.9 | — | 86.9–91.0 |

TABLE 1-continued

Sequence comparisons of HAV strain AGM-27 and other HAV strains[a]

| Genome region | Length | | | | *Identity versus AGM-27 | | | |
|---|---|---|---|---|---|---|---|---|
| | Nucleotides | | Amino acids | | Nucleotides[b] | | Amino acids[c] | |
| | AGM-27 | others | AGM-27 | others | PA21 | human | PA 21 | human |
| 3A | 216 | 216–222 | 72 | 72–74 | — | 79.2–83.8 | — | 86.1–88.9 |
| 3B | 69 | 69 | 23 | 23 | — | 75–80 | — | 95.7 |
| 3C | 660 | 657 | 220 | 217 | — | 81.9–83.4 | — | 95.9–96.3 |
| 3D | 1467 | 1467 | 489 | 489 | — | 81.5–81.9 | — | 90.4–91.0 |
| 3'NT | 64 | 63–64 | — | — | — | 75–89 | — | — |

[a]Other HAV strains: HM–175(Cohen, J.I., et al. (1987) J. Virol. 61:50–59), CR326(Linemeyer, D.L., et al. (1985) J. Virol. 54:247–255), HAS15 (Sverdlov, E.D., et al. (1987) Mol. Gen. (Life Sci. Adv.) 6:129–133), LA (Najarian, R.D., et al. (1985) Proc. Natl. Acad. Sci. USA. 82:2627–2631), MBB (Paul, A.V., et al. (1987) Virus Research 8:153–171) of human origin, and, PA 21, of probable simian origin (Brown, E.A., et al. (1989) J. Virol. 63:4932–4937).
[b]Compared by computer programs for global alignment ("GAP") and multiple sequence alignment ("DISTANCES") from the GCG Sequence Analysis Software Package (Devereux, J., et al. (1984) Nucl. Acids. Res. 12:387–395).
[c]Compared by using a computer program for global alignment ("SEQAP") from the IDEAS software package (Goad, W.B., et al. (1982) Nucleic Acids Res. 10:247–263).
[d]Approximate. The sequence determined for AGM-27 starts from nucleotide 59 according to the nomenclature for HM 175 (Cohen, J.I., et al. (1987) J. Virol. 61:50–59). Between nucleotide 116 and 136 a stretch of oligo T is present. The exact number of T in the stretch is not known: from 10 plasmids sequenced one contained 11 T, two-12 T, two-13 T, one-12 T and 1 C after the 5th T, one -15 T, one - 16T, one -17 T, one -22 T and 1 C after the 10th T. To make a continuous AGM-27 assumed that it had 18 Ts in the ambiguous region.

EXAMPLE 2

Growth of AGM-27 in cell cultures

Figure 4:
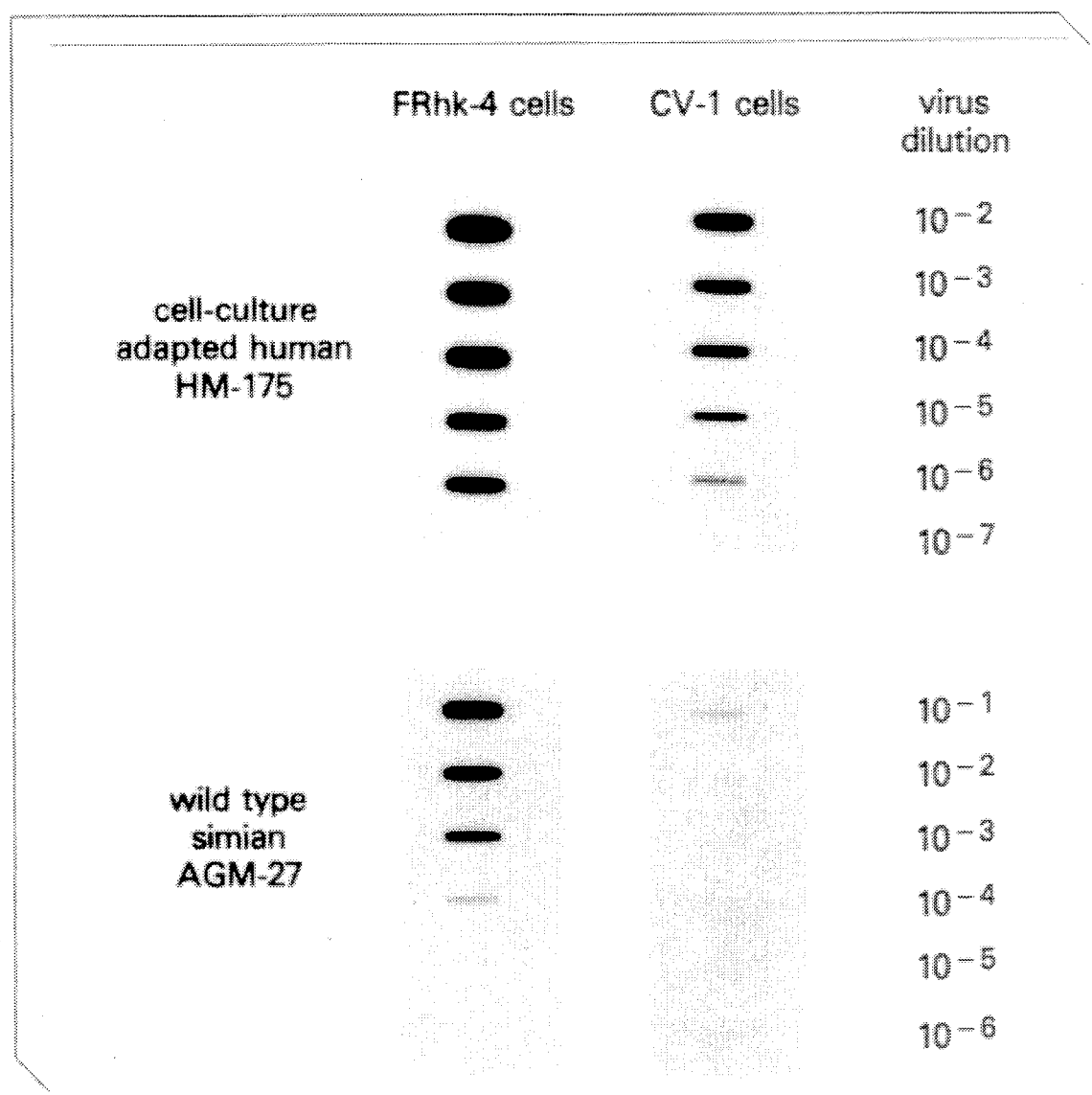
FIG. 4. Comparison of growth of simian and human HAV in two different cell lines. Equal aliquots of serially diluted samples containing either the cell culture-adapted variant of HM-175 or the wild-type AGM-27 viruses were plated on confluent cell monolayers of CV-1 or FRhK-4 cells. After 20 days incubation, cells were lysed and viral replication was quantified by slot-blot (Ticehurst, J.R., et al. (1987) J. Clin. Microbiol. 25:1822–1829) to determine the titration end point.

FRhK-4 and CV-1 cell lines were inoculated with 10-fold dilutions of 10% liver homogenate containing AGM-27. Preliminary experiments had shown that growth of AGM-27 could be detected by day 14 in either primary African green monkey kidney (AGMK) or FRhK-4 cells by immunofluorescence and slot blot assays. Therefore, virus replication after 20 days was assayed by slot blot and radioautography (FIG. 4). The AGM-27 virus grew well, even when diluted as much as $10^{-4}$, in FRhK-4 cells but replication in CV-1 cells was not detected. In comparison, cell culture-adapted HM-175 strain grew relatively well in both cell cultures: growth was detected in both cultures when the inoculum was diluted $10^{-6}$ and in neither culture when the inoculum was diluted $10^{-7}$.

EXAMPLE 3

Use of AGM-27 as a Vaccine

Figure 5A:
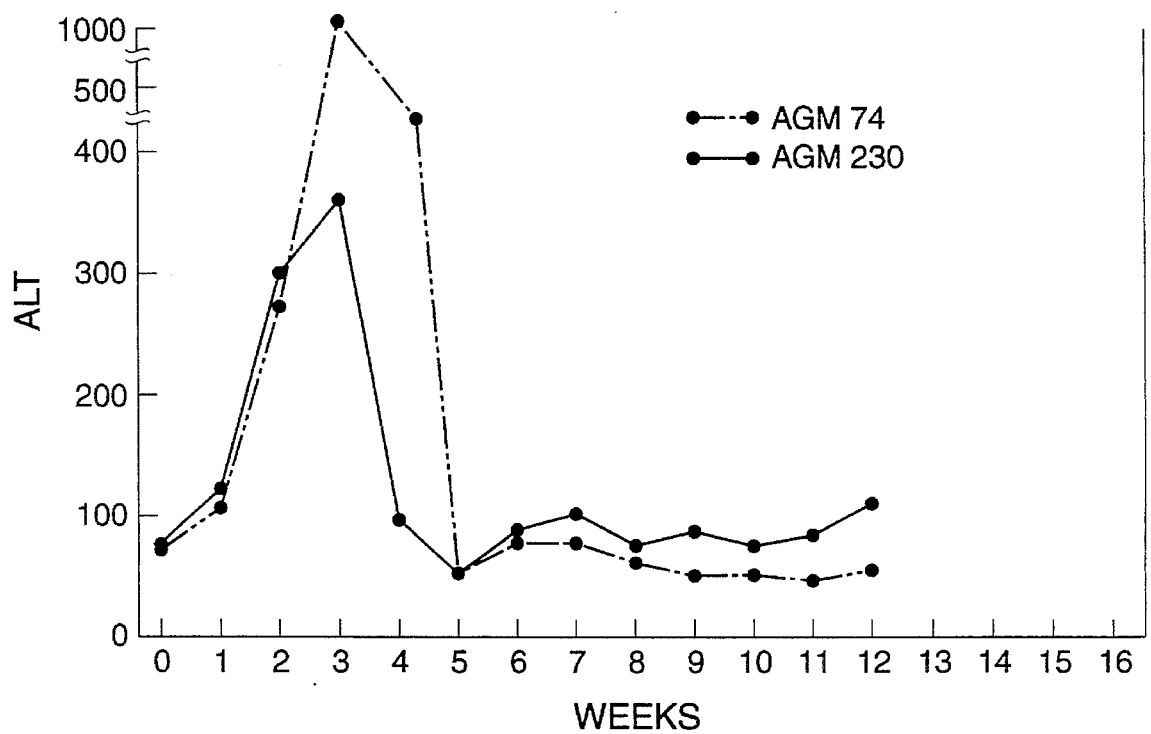
FIGS. 5A–5C show Transmission of HAV (Strain AGM-27) to primates where
Figure 5B:
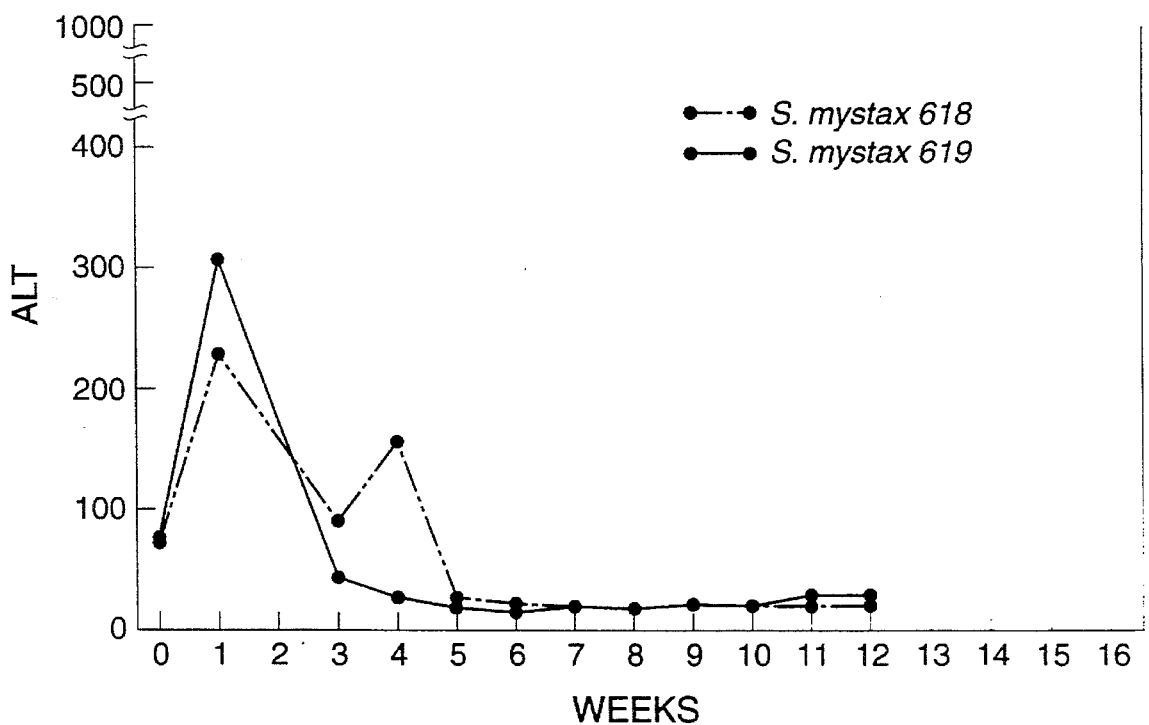
Figure 5C:
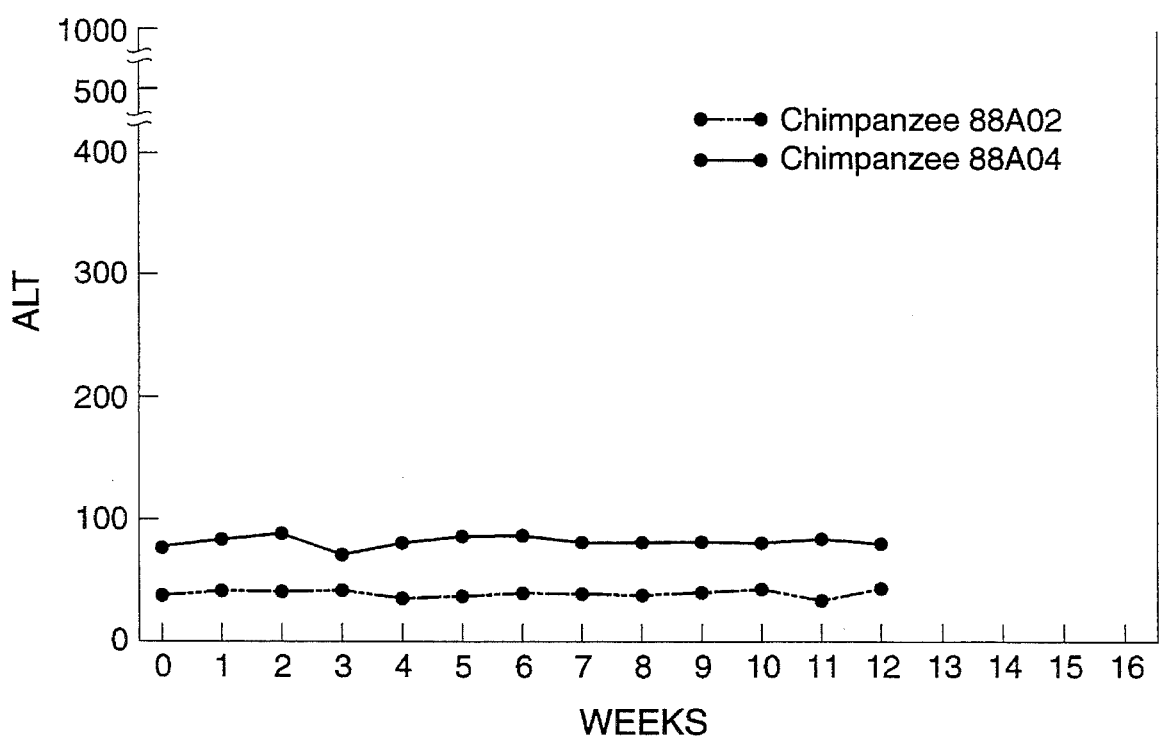

Cross-protection experiments based on immunization of chimpanzees with AGM-27 virus followed by challenge with human virulent HAV are currently under way. Infection of 2 chimpanzees with AGM-27 (FIG. 5C) has resulted in animals with high titers of anti-HAV antibodies and no sign of disease. In contrast, two African green monkeys (AGM) FIG. 5C and two marmoset monkeys (*S. mystrx*) (FIG. 5B) developed hepatitis when administered the same inoculum parenterally. Therefore, this simian strain behaves similarly to human attenuated strain HM-175 in chimpanzees, but not in marmosets.

EXAMPLE 4

Construction of Chimeras

Chimeras can be constructed by religation of purified cDNA fragments generated by digestion with restriction enzymes. A chimera HAV has been constructed between human and simian strains using the enzymes Sac I and EcoRI (FIG. 6). Segments will also be exchanged using PCR generated single-stranded DNA as a mutagenic oligonucleotide (Wychowski, C. et al (1990) Nucleic Acids Res. 18:913–918).

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 7400 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:1:

```
CTTGATACCT CACCGCCGTT TGCCTAGGCT ATAGGCTTCT TCCCTACACC CTTGTTTGTT      60
TTTTTTTTTT TTTTTGTGT  GTTTGTAAAT ATTAATTCCT GCAGGTTCAG GGTTCTTAAT     120
TTGTTCTGCT ATACAGACAC TCTTTTCACG CTTTCTGTCA TCTTATTTCC TGGGCTCTCC     180
CCTTGCCCAA GGCTCTGGCC GTTGCGCCCG GCGGGGTCAA CTCCATGGTT AGCATGGAGC     240
TGTAGGAGTC TAAATTGGGG ACGCAGATGC TAGGAACGTC GCCCTGCAGT GTTAACCTGG     300
CTTTCATGAA GCTCTTTGAT CTTCTACAAG AGGTAGGCTA CGGGTGAAAC CTCTTAGATT     360
AATACTCCTA TGGAGAGATA TCTTGAATAG GGTAACAGCG GTGGATATTG GTGAGTTCCT     420
TTGGGACAAA AACCATTCAA CACCGGAGGA CTGACTCTCA TTCAGTAGTT GCATTGAGTG     480
AATTGTCTGT CAGGGCTGTC TTTGGGTTTA ATTCCTGGCC TCTCTGTGCT TAGGGCAAAC     540
CATTTCCTGG CCTTAAATGG AGTTCTGTGA GAGGGAACTC CTCCTTTATA TGCTGGACAT     600
ATTTGGGGC  CTTAGGGTTA TGGTTTGCCT CTGAGGTACT CAGGGCATT  TAGGTTTTTC     660
CTCATTTATA TGTTATGAT  GATGAATATG TCTAAACAAG GTATTTCCA  GACTGTGGG     720
AGTGGCCTTG ACCACATACT GTCTTTAGCA GATGTGGAGG AAGAGCAAAT GATACAGTCA     780
GTGGACAGGA CAGCTGTCAC TGGTGCTTCT TATTTACTT  CTGTAGACCA ATCTTCAGTT     840
CATACGGCAG AAGTTGGTGC ACATCAGACA GAGCCTCTTA AGACATCAGT AGATAAACCA     900
GGTTCAAAGA AAACCCAAGG AGAGAAATTT TTCCTAATAC ATTCTGCAGA TTGGTTAACA     960
ACACATGCTT TGTTTCATGA AGTCGCCAAA TTGGATGTTG TTAGTTTGTT GTACAATGAA    1020
CAATTTGCTG TACAGGGTTT GTTGAGATAC CATACTTATG CTAGATTTGG AATTGAAATT    1080
CAAGTCCAGA TTAATCCCAC TCCCTTTCAG CAGGGAGGTC TTATTTGTGC AATGGTTCCA    1140
GGAGACCAAG GTTATGGTTC CATAGCCTCA TTGACAGTTT ATCCACATGG TCTCTTGAAT    1200
TGCAACATTA ACAATGTTGT TAGAATCAAA GTTCCATTCA TTTATACTAG AGGTGCTTAT    1260
CATTTCAAAG ATCCACAGTA TCCAGTCTGG GAGTTAACTA TTCGTGTTTG GTCAGAATTA    1320
AATATAGGAA CTGGTACTTC TGCTTATACA TCATTGAATG TCTTGGCTAG ATTCACTGAT    1380
TTAGAGCTTC ATGGATTGAC ACCATTATCT ACACAAATGA TGAGGAATGA ATTTAGAGTG    1440
AGTACAACTG AAAATGTGGT TAATTTGTCA AATTACGAGG ATGCTAGAGC AAAGATGTCT    1500
TTTGCACTTG ATCAGGAAGA TTGGAAAACA GATCCCTCGC AAGGAGGAGG AATCAAAATC    1560
ACTCATTTTA CAACATGGAC TTCAATTCCC ACGCTTGCTG CACAGTTTGC ATTTAATGCT    1620
TCTGCATCTG TGGGGCAGCA AATTAAGGTG ATCCCTGTTG ATCCTTATTT TTATCAGATG    1680
ACCAATTCAA ATCCAGACCA AAAGTGTATT ACTGCTTTAG CTTCTGTCTG TCAGATGTTC    1740
TGCTTTTGGA GGGGAGATCT TGTTTTTGAT TTTCAGGTTT TCCCCACAAA ATATCACTCT    1800
GGGAGGTTGT TATTTGTTT  TGTGCCAGGG AATGAGTTGA TAGATGTTTC AGGTATAACC    1860
```

| | | | | | |
|---|---|---|---|---|---|
| CTGAAGCAGG | CAACTACTGC | ACCCTGTGCT | GTTATGGATA | TAACAGGAGT | TCAGTCAACA | 1920 |
| TTGAGATTTA | GAGTGCCTTG | GATCTCTGAT | ACACCTTACA | GAGTGAATAG | ATACACAAAA | 1980 |
| TCAGCTCACC | AGAAAGGAGA | GTATACAGCT | ATTGGGAAGT | TGATTGTTTA | TTGTTATAAT | 2040 |
| AGGCTTACCT | CACCCTCAAA | TGTTGCTTCC | CATGTTAGGG | TTAATGTTTA | TCTTTCTGCA | 2100 |
| ATAAATTTGG | AATGTTTGC | ACCCTATAT | CATGCAATGG | ATGTGACATC | ACAGACAGGT | 2160 |
| GATGATTCAG | GTGGGTTTTC | AACTACAGTT | TCTACAGAAC | AGAATGCTCC | TGATCCTCAA | 2220 |
| GTTGGAATTA | CCACTATTAA | GGATTAAAA | GGGAAGGCAA | ATAGAGGAAA | GATGGATGTT | 2280 |
| TCTGGCATTC | AAGCACCAGT | GGGTGCTATT | ACAACCATTG | AGGATCCAGT | GTTAGCTAAA | 2340 |
| AAAGTTCCTG | AGACTTTTCC | AGAATTGAGA | CCAGGTGAAT | CTAGACATAC | TTCAGATCAT | 2400 |
| ATGTCTATTT | ACAAATTTAT | GGGGAGGTCA | CACTTTCTTT | GTACATTTAC | TTTCAATGCA | 2460 |
| AACAATAGGG | AGTATACTTT | TCCAATAACA | CTGTCCTCTA | CATCGAATCC | ACCTCATGGT | 2520 |
| TTACCATCAA | CACTGAGGTG | GTTTTCAAC | CTTTTCAAT | TGTATAGAGG | GCCATTGGAC | 2580 |
| TTGACTATTA | TAATTACAGG | TGCTACTGAT | GTGGATGGCA | TGGCTTGGTT | TACTCCTGTG | 2640 |
| GGCCTAGCTG | TGGATACTCC | CTGGGTTGAA | AAGCAATCAG | CGTTGACTAT | TGATTATAAA | 2700 |
| ACTGCTCTTG | GGCTATTAG | GTTAACACT | AGGAGAACAG | GAAATATTCA | GATTAGACTT | 2760 |
| CCTTGGTATT | CATACCTTTA | TGCTGTTTCT | GGCGCTTTGG | ATGGACTTGG | GGACACTACT | 2820 |
| GATTCGACTT | TCGGGTTGGT | CTCTATTCAG | ATTGCCAATT | ATAATCATTC | AGATGAATAT | 2880 |
| CTGTCATTCA | GTTGTTATCT | TTCAGTTACT | GAACAATCAG | AATTTTATTT | TCCAAGGGCT | 2940 |
| CCTCTCAATT | CTAATGCTAT | GATGGTTTCT | GAGTCCATGC | TAGATCGCAT | TGCAAGTGGA | 3000 |
| GATTAGAAT | CATCAGTTGA | TGACCCAAGA | TCAGCAGAGG | ACAAAAGGTT | TGAAAGTCAT | 3060 |
| ATTGAGCAGG | GCAAGCCATA | CAAAGAATTA | AGAATGGAAG | TTGGGAAGCA | GAGATTGAAA | 3120 |
| TATGCCATGG | AGGAGTTATC | AAATGAAATT | TTACCACCTC | CTCGGAAAGT | GAAAGGACTG | 3180 |
| TTTTCTCAAG | CTAAAATTTC | TTTATTTTAT | ACAGAAGACC | ATGAAATTGT | GAAGCTTTCA | 3240 |
| TGGAAAGGTC | TCACAGCTGA | TACAAGAGCT | CTCAGGAGAT | ATGGTTTTTC | TCTTGCTGCT | 3300 |
| GGAAGAAGTG | TGTGGACTCT | TGAGATGGAA | GCTGGAGTTC | TGACTGGAAG | GATGATCAGA | 3360 |
| TTGAATGATG | AAAAGTGGAC | TGAGATTAAG | GATGATAAGA | TAGTGGCTTT | GGTAGAGAAA | 3420 |
| TTTACATCTA | ATAAGAATTG | GTCTAAAGTC | AATTTTCCAC | ATGGGATGCT | AGATTTGGAA | 3480 |
| GAGATAGCAT | CAAATTCAAA | GGATTTTCCT | AATATGTCTG | AGACTGACTT | GTGTTTTCTT | 3540 |
| TTACATTGGT | TGAATCCTAA | GAAGATAAAT | CTAGCTGATA | GAATGCTTGG | ATTGTCTGGT | 3600 |
| GTTCAGGAAA | TTAAGGAACA | GGGTGTTGGC | TTAATAGCTG | AATGTAGAAC | ATTTTAGAT | 3660 |
| TCTATAGCTG | GCACTTTGAA | ATCAATGATG | TTTGGGTTTC | ATCAGTCTGT | TACTGTGGAA | 3720 |
| ATAATTAATA | CTGTCTTGTG | TTTTGTTAAG | AGTGGGATCC | TTCTTTATGT | TATTCAGCAA | 3780 |
| TTGAATCAAA | ATGAACACTC | TCATATTATA | GGGCTTTTAC | AGGTGATGAA | TTATGCAGAC | 3840 |
| ATTGGTTGCT | CTGTGATTTC | TTGTGGAAAG | ATATTCTCAA | AAATGTTAGA | AACAGTCTTT | 3900 |
| AATTGGCAGA | TGGATTCTAG | AATGATGGCT | CTTAGAACAC | AGAGTTTCTC | TAATTGGTTG | 3960 |
| AGAGACATAT | GTTCGGGGAT | AACCATTTTC | AAAAATTTTA | AGGATGCTAT | TTTCTGGCTG | 4020 |
| TACACTAAAT | TAAAGGATTA | TTATGATTCT | AACTATGGGA | AAAAGAAGGA | TGTTCTGAAT | 4080 |
| GTTTTAAAAG | AAAATCAGCA | TAGGATTGAG | AAAGCCATTG | AAGAGGCTGA | TCAGTTCTGT | 4140 |
| GTTTTGCAGA | TTCAGGACGT | TGAGAAGTCA | GAGCAATATC | AGAAGGGAGT | TGAACTCATT | 4200 |

```
CAGAAATTGA  GAACAGTTCA  TTCCCTGGCC  CAGGTCGACT  CTAGTTTGAT  GTCTCATTTG    4260
TCACCACTGA  GAGATTGTAT  TGCTAGAGTC  CATCAAAAAC  TTAAGAATTT  AGGCTCAATT    4320
AATCAGGCTA  TGGTGACTAG  GTGTGAACCT  GTGGTCTGTT  ATTTATATGG  TAAGAGAGGT    4380
GGAGGAAAGA  GTTTAACTTC  TATTGCATTG  GCAACAAAAA  TTTGCAAACA  TTATGGTGTT    4440
GAACCAGAAA  AGAATATATA  TACAAAACCT  GTTGCTTCAG  ACTACTGGGA  TGGATATAGT    4500
GGTCAATTGG  TTTGTATCAT  TGATGACATT  GGTCAAAATA  CTACAGATGA  AGATTGGTCA    4560
GATTTTGTC   AATTGGTGTC  TGGTTGTCCT  ATGAGGTTAA  ATATGGCTTC  TTTGGAAGAG    4620
AAAGGGAGAC  ACTTTTCTTC  CCCGTTTATA  ATTGCCACAT  CAAATTGGTC  AAATCCAAGT    4680
CCTAAGACTG  TTTATGTGAA  GGAAGCTATA  GATCGCCGCC  TTCATTATAA  GATTGAAGTC    4740
AAACCAGCAT  CTTTTTACAA  AAATGCACAC  AATGATATGC  TCAATGTGAA  TCTTGCAAGA    4800
AATAATGATG  CCATTAAAGA  CATGTCCTGT  GTAGATTTAC  TGATGGATGG  CCATACTGTG    4860
TCTTTATCTG  AGCTTTTAAA  TTCTCTTGTT  ATGACAGTTG  AAATTAGAAA  ACAAAATATG    4920
TCAGAATTTA  TGAAATTGTG  GTCACAGGGT  GTGTCAGATG  ATGATAATGA  CAGTGCAGTT    4980
GCTGAGTTCT  TCCAGTCTTT  TCCATCAGGA  GAACCCTCAA  ATTCTAAGTT  ATCTAGTTTC    5040
TTCAAGGCGG  TCACTAATCA  TAAGTGGGTT  GCTATTGGAG  CTGCTGTTGG  AGTTCTGGGT    5100
GTCTTAGTGG  GAGGTTGGTT  TGTGTACAAG  CATTTTACCA  AGAAGAACC   AATACCAACT    5160
GAAGGAGTGT  ATCATGGAGT  AACCAAACCT  AAACAGGTTA  TCAAATTGGA  TGCTGATCCT    5220
GTTGACTCCC  AATCTACTCT  TGAGATAGCT  GGACTAGTTA  GGAAGAATTT  GGTTCAATTT    5280
GGAGTTGGGG  AGAAGAATGG  ATGTGTTAGG  TGGGTCATGA  ATGCTTAGG   TATTAAAGAT    5340
GATTGGCTGC  TGGTCCCCTC  ACATGCATAC  AAATTTGAGA  AAGATTATCA  AATGATGGAG    5400
TTTTATTTTA  ATAGAGGAGG  AACTTATTAT  TCAATTTCTG  CTGGTAATGT  TGTAATCCAG    5460
TCTTTGGATG  TTGGTTTTCA  GGATGTTGTT  TTGATGAAGG  TTCCTACAAT  TCCAAAGTTT    5520
AGAGATATAA  CTGAGCATTT  TATTAAGAAG  AATGATGTTC  CAAGAGCTTT  GAATAGATTG    5580
GCTACACTTG  TTACAACAGT  TAATGGGACA  CCAATGCTGA  TTTCCGAAGG  TCCACTTAAG    5640
ATGGAAGAAA  AGGCCACTTA  TGTCCATAAG  AGAAATGACG  GAACTACTGT  TGATTTGACT    5700
GTTGATCAAG  CTTGGAGGGG  AAAAGGTGAG  GGCCTCCCAG  GTATGTGTGG  TGGAGCTCTG    5760
ATTTCCTCAA  ATCAGTCAAT  ACAAAATGCC  ATTCTTGGGA  TTCATGTTGC  AGGTGGCAAT    5820
TCTATTTTGG  TTGCCAAACT  TGTGACTCAG  GAAATGTTCC  AGAACATTGA  ACAAAAAGCA    5880
ATAGAAAGTC  AGAGGATAAT  GAAAGTGGAA  TTCACTCAGT  GTTCAATGAA  TGTGGTCTCC    5940
AAAACGCTTT  TTAAAAAGAG  TCCAATTCAT  CATCACATTG  ATAGGAACAT  GATTAATTTT    6000
CCTGCTGTAA  TGCCTTTTTC  TAAAGCTGAG  ATTGATCCTA  TGGCTGTTAT  GTTGTCTAAG    6060
TATTCTCTTC  CTATTGTTGA  AGAGCCAGAT  GATTATAAGA  TGGCTTCCAT  TTATTTCCAA    6120
AATAAAGTAA  TGGGGAAAAC  TTTTCTTGTT  GATGACTTTT  GGATATAGA   TATGGCAATC    6180
ACAGGTGCTC  CAGGAATAGA  TGCTATTAAT  ATGGATTCTT  CACCAGGATT  TCCTTATGTT    6240
CAGGAGAAGT  TGACAAAGAA  AGACTTGATC  TGGTTGGATG  AGAATGGGCT  GCTGTTAGGA    6300
GTTCATCCAA  GGCTTGCTCA  AGAATCTTG   TACAACACAG  TTATGATGGA  GAATTGTTCT    6360
GATCTTGATG  TGGTCTTTAC  AACATGTCCC  AAGGATGAAC  TTAGGCCTCT  GGACAAAGTA    6420
TTGGAATCAA  AGACTAGAGC  AATTGATGCT  TGTCCATTGG  ATTATACAAT  TCTTTGTAGG    6480
ATTTATTGGG  GTCCTGCTAT  TAGTTACTTT  CAATTGAATC  CTGGATTTCA  CACAGGAGTT    6540
GCTATTGGAA  TTGATCCGGA  TAGACATTGG  GACGAGTTGT  TTAAAACAAT  GGTTAGATTT    6600
```

-continued

| | | | | | | |
|---|---|---|---|---|---|---|
| GGTGATGTAG | GTTTAGACCT | TGATTTTTCA | TCATTTGATG | CTAGTCTTAG | TCCTTTTATG | 6660 |
| ATAAGAGAGG | CAGGGAGAAT | TTTGAGTGAA | ATGTCAGGGA | CACCCTCACA | CTTTGGAGAG | 6720 |
| GCCTTGATTA | ATACAATCAT | TTATTCCAAG | CATTTGTTGT | ACAATTGTTG | TTATCATGTT | 6780 |
| TATGGTTCCA | TGCCATCAGG | GTCCCCTTGT | ACAGCACTTT | TAAATTCAAT | TGTAAACAAT | 6840 |
| GTTAATTTGT | ACTATGTGTT | TTCAAAAATT | TTTAGGAAGT | CTCCTGTTTT | CTTTGGAGAT | 6900 |
| GCTCTGAAGA | TTCTTTGTTA | TGGAGATGAT | GTCCTCATTG | TTTTTTCCAG | AAATGTCCAG | 6960 |
| ATTGATAATT | TGGAATCTAT | TGGACAGAAA | ATTGTAGATG | AGTTGGAAA | ATTAGGCATG | 7020 |
| ACTGCAACAT | CAGCAGACAA | GTCTGTTCCT | AAGTTGAAAC | CTATTTCTGA | GCTCACTTTT | 7080 |
| CTTAAAAGAT | CATTCAATCT | TGTTGAAGAT | CGGATTAGAC | CTGCAATTTC | AGAGAAAACA | 7140 |
| ATTTGGTCTC | TCGTTGCTTG | GCAGAGAAGC | AATGCTGAAT | TTGAACAGAA | TTTGGAAAAT | 7200 |
| GCTCAATGGT | TTGCTTTTAT | GCATGGTTTT | GAATTTATC | AGAAATTTTA | CCATTTTGTT | 7260 |
| CAGTCCTGCC | TGGAGAAAGA | GATGGTAGAA | TACAGATTGA | AATCATATGA | TTGGTGGAGA | 7320 |
| ATGAAGTTTT | ATGATCAGTG | CTTTGTTTGT | GACCTCACAT | GATTTGTTTA | AACAAACCTT | 7380 |
| CTTAAAATTT | CTGAGATTTG | | | | | 7400 |

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A pharmaceutical composition comprising simian hepatitis A vital isolate AGM-27 in an amount effective to provide humans or apes with protective immunity to hepatitis A, and a pharmaceutically acceptable diluent, carrier or excipient.

2. A method for preventing hepatitis A in humans or apes comprising administering to said humans or apes simian hepatitis A vital isolate AGM-27.

3. A vaccine comprising simian hepatitis A vital isolate AGM-27 in an amount effective to provide.

4. A method of producing antibodies to hepatitis A virus in an animal comprising administering to said animal simian hepatitis A viral isolate AGM-27.

5. The method of claim 4, wherein said animal is selected from the group consisting of humans, apes and monkeys.

6. A pharmaceutical composition comprising simian hepatitis A viral isolate AGM-27 where said isolate is in an amount effective to produce antibodies to hepatitis A in an animal, and a pharmaceutically acceptable diluent, carrier or excipient.

* * * * *

UNITED STATES PATENT AND TRADEMARK OFFICE
CERTIFICATE OF CORRECTION

PATENT NO. : 5,476,658
DATED : December 19, 1995
INVENTOR(S) : Sergei A. Tsarev, Suzanne U. Emerson, Michael S. Balayan and Robert H. Purcell It is certified that error appears in the above-indentified patent and that said Letters Patent is hereby corrected as shown below:

Claim 1, column 15, line 38, delete "vital" and insert --viral--.

Claim 2, column 15, line 44, delete "vital" and insert --viral--.

Claim 3, column 16, line 29, delete "vital" and insert --viral--.

Claim 3, column 16, line 30, after "provide", insert --humans or apes with protective immunity to hepatitis A, and a pharmaceutically acceptable diluent, carrier or excipient--.

Signed and Sealed this

Sixth Day of August, 1996

*Attest:*

Bruce Lehman

BRUCE LEHMAN

*Attesting Officer*    *Commissioner of Patents and Trademarks*